(12) United States Patent
Mukai

(10) Patent No.: US 8,821,936 B2
(45) Date of Patent: Sep. 2, 2014

(54) SOLID PHARMACEUTICAL FORMULATION

(75) Inventor: Tadashi Mukai, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 432 days.

(21) Appl. No.: 11/596,219

(22) PCT Filed: May 19, 2005

(86) PCT No.: PCT/JP2005/009583
§ 371 (c)(1),
(2), (4) Date: Nov. 14, 2006

(87) PCT Pub. No.: WO2005/113009
PCT Pub. Date: Dec. 1, 2005

(65) Prior Publication Data
US 2008/0033009 A1    Feb. 7, 2008

(30) Foreign Application Priority Data

May 20, 2004    (JP) ............................... 2004-150557

(51) Int. Cl.
| | | |
|---|---|---|
| A61K 9/00 | (2006.01) | |
| A61K 31/47 | (2006.01) | |
| A61K 47/00 | (2006.01) | |
| A61K 9/62 | (2006.01) | |
| A61K 9/36 | (2006.01) | |
| A61K 9/22 | (2006.01) | |

(52) U.S. Cl.
USPC ........... 424/489; 424/400; 424/461; 424/480; 424/484; 424/488; 514/312; 514/778; 514/781

(58) Field of Classification Search
USPC ......... 424/464, 400, 461, 480, 484, 488, 489; 514/312, 778, 781
See application file for complete search history.

(56) References Cited

U.S. PATENT DOCUMENTS

| | | | | |
|---|---|---|---|---|
| 4,266,348 | A | * | 5/1981 | Ledding .......................... 34/368 |
| 4,755,397 | A | | 7/1988 | Eden et al. |
| 5,073,380 | A | | 12/1991 | Babu et al. |
| 5,132,116 | A | | 7/1992 | Sournac et al. |
| 5,334,393 | A | | 8/1994 | Bougaret et al. |
| 6,129,932 | A | * | 10/2000 | Asgharnejad et al. ........ 424/489 |
| 6,287,596 | B1 | | 9/2001 | Murakami et al. |
| 6,303,147 | B1 | * | 10/2001 | Gilis .............................. 424/484 |
| 6,388,080 | B1 | | 5/2002 | Stowell et al. |
| 6,509,040 | B1 | | 1/2003 | Murray et al. |
| 6,515,128 | B2 | | 2/2003 | Mendelovici et al. |
| 6,531,603 | B1 | | 3/2003 | Stowell et al. |
| 6,669,957 | B1 | | 12/2003 | Laruelle et al. |
| 7,138,143 | B1 | | 11/2006 | Mukai et al. |
| 7,144,585 | B1 | | 12/2006 | Mukai et al. |
| 2002/0058066 | A1 | | 5/2002 | Tomohira et al. |
| 2003/0045549 | A1 | | 3/2003 | Stowell et al. |
| 2003/0176703 | A1 | | 9/2003 | Mendelovici et al. |
| 2005/0255155 | A1 | * | 11/2005 | Sen et al. ....................... 424/451 |

FOREIGN PATENT DOCUMENTS

| | | |
|---|---|---|
| EP | 0 280 613 | 8/1988 |
| EP | 1161941 A1 | 12/2001 |
| EP | 1 396 266 A1 | 3/2004 |
| GB | 825892 | 12/1959 |
| GB | 2 195 893 | 4/1988 |
| JP | 08-325146 | 12/1996 |
| JP | 10-182701 A | 7/1998 |
| JP | 11-286456 | 10/1999 |
| JP | 2001-163769 | 6/2001 |
| JP | 2002-193792 | 7/2002 |
| WO | WO 96/21448 | 7/1996 |
| WO | WO 97/04752 | 2/1997 |
| WO | WO 97/24109 | 7/1997 |
| WO | WO 98/18610 | 5/1998 |
| WO | WO 99/56666 | 11/1999 |
| WO | WO 00/59477 | 10/2000 |
| WO | WO 0057881 A1 * | 10/2000 |
| WO | WO 2004/039361 A1 | 5/2004 |

OTHER PUBLICATIONS

Howard Ansel, Introduction to Pharmaceutical Dosage Forms, Chapter 89, 1985, Lea and Febiger, Fourth Edition, pp. 1642-1643.*
Asahi Kasei Chemicals, "Pregelatinized starch PCS", internet article, Oct. 2004, [retrieved on Sep. 24, 2013], retrieved from the Internet: URL:http://web.archive.org/web/20041014112730/http://www.ceolus.com/eng/product/pcs/index.html, 3 pages.*
International Preliminary Examination Report dated Nov. 30, 2006.
Notice of Opposition of Pakistan Patent No. 140102 dated Nov. 20, 2009.
Supplementary European Search Report for EP Application No. 05743223.9-1219 dated Oct. 9, 2012.
Office Action for Indian Counterpart Application No. 7008/DELNP/2006 dated Apr. 5, 2011.

* cited by examiner

*Primary Examiner* — John Pak
*Assistant Examiner* — Andriae M Holt
(74) *Attorney, Agent, or Firm* — Finnegan, Henderson, Farabow, Garrett & Dunner, L.L.P.

(57) ABSTRACT

This invention provides a solid pharmaceutical formulation having high physical strength and further having excellent drug release properties and digestibility of excipients when administered, which comprises (a) an active medical ingredient and (b) a pre-gelatinized starch in an amount of 10 to 90% by weight, said pre-gelatinized starch being prepared by pre-gelatinizing a cheap and stable usual starch during the procedure for formulation. This invention also provides a method for preparing the solid pharmaceutical formulation.

5 Claims, 3 Drawing Sheets

SOLID PHARMACEUTICAL FORMULATION

TECHNICAL FIELD

The present invention relates to a solid pharmaceutical formulation, more particularly, it relates to a solid pharmaceutical formulation having high physical strength, which is excellent in drug release properties and in digestibility of the excipients when administered. The present invention also provides a method for preparing the solid pharmaceutical formulation.

BACKGROUND ART

Solid pharmaceutical formulation comprises usually an active ingredient in admixture with pharmaceutically acceptable excipients, said excipients being used in order to improve the easiness of administration of the drug and also to improve the formability of the formulation (cf. JP-A-11-286456). Hitherto, there has been usually used starch as an excipient for solid pharmaceutical formulations. Starch has advantageously been used as an excipient for pharmaceutical formulation because of excellent stability and safety and further when it is used as a carrier for granules prepared by extrusion granulation technique, it improves plasticity of the granules owing to water-retentivity thereof, and thereby alleviates the burden onto the screen of extrusion granulator and gives easier procedure of the granulation step.

On the other hand, starch has physical properties that the particles thereof are hard and have round shape in dry state, and hence when usual starch is used as an excipient for solid pharmaceutical formulation, the formed solid formulation has inferior physical strength. The less strength of solid pharmaceutical formulation is likely to cause breakage failure of the solid formulation and hence cause of lower yield of the product and lower efficiency in packaging step thereof. Accordingly, it is required to improve the physical strength of the solid pharmaceutical formulation when usual starch is used as an excipient for solid pharmaceutical formulation.

Moreover, the solid pharmaceutical formulation prepared by using usual starch as an excipient is also insufficient in drug release properties when administered, and hence, it is also required to modify the formulation so that the drug is rapidly released in the digestive tract.

By the way, it is known that pre-gelatinized starch ($\alpha$-starch) has properties to become pasty when mixed with water, and by utilizing the properties, the pre-gelatinized starch is usually added as a binder in a small amount for preparing a solid pharmaceutical formulation. The pre-gelatinized starch has superior digestibility within digestive tract in comparison with usual starch and is easily digested within digestive tract, and hence it is preferable for incorporating into solid pharmaceutical formulations.

However, when the pre-gelatinized starch is incorporated as an excipient in a large amount into the solid pharmaceutical formulation, the mixture becomes pasty when it is subjected to wet-granulation, which causes difficulty in the preparation of the pharmaceutical formulation. Further, even when the pasty mixture of the pre-gelatinized starch and an active medical component is dried, it becomes undesirably a hard aggregated product, which is difficult to pulverize for preparing pharmaceutical formulation.

It has never been known to prepare a solid pharmaceutical formulation by a hydrolytic granulation technique using a pre-gelatinized starch, and there has not yet been established a technique of preparing a pharmaceutical formulation containing a pre-gelatinized starch in a ratio of about 10% by weight or more and having the desired strength.

DISCLOSURE OF INVENTION

An object of the present invention is to solve the above-mentioned problems involved in the solid pharmaceutical formulation containing a pre-gelatinized starch as an excipient. In more specifically, an object of the present invention is to provide a solid pharmaceutical formulation having excellent physical strength and having excellent drug release properties when administered by using inexpensive and safe starch as an excipient. A further object of the present invention is to provide a method for preparing a solid pharmaceutical formulation incorporated with a pre-gelatinized starch as an excipient.

As a result of the present inventors' extensive studies, it has been found that when an active medicament is mixed with usual starch and the mixture is formulated, and then it is subjected to the treatment for pre-gelatinization of starch by which the starting usual starch is converted into alpha-starch ($\alpha$-starch), the resulting solid pharmaceutical formulation has high physical strength and are excellent in the drug release properties and also excellent in digestibility of the excipient when administered. The present invention has been completed on the basis of the above new-finding.

Thus, the present invention provides a solid pharmaceutical formulation containing a pre-gelatinized starch ($\alpha$-starch) as a binder, wherein the starting usual starch is pre-gelatinized after formulating with an active ingredient as well as other pharmaceutically acceptable carriers into a pharmaceutical composition, followed by drying, by which specific procedure the desired solid pharmaceutical composition having excellent properties can be obtained without disadvantageous phenomena such as pastiness during the wet granulation step or forming a hard aggregated product in the drying step.

The present invention includes the following features of solid pharmaceutical formulation.

1. A solid pharmaceutical formulation which comprises (a) an active medical ingredient and (b) a pre-gelatinized starch in an amount of 10 to 90% by weight based on the whole weight of the formulation.

2. The solid pharmaceutical formulation as set forth in the above 1, which is prepared by the following steps (i) and (ii):
(i) a step of mixing an active medical ingredient and a starting usual starch to prepare a starting composition, and
(ii) a step of subjecting the starting composition to a pre-gelatinization of starch.

3. The solid pharmaceutical formulation as set forth in the above 2, wherein the starting composition prepared in the step (i) further comprises crystalline cellulose and is granulated by an extrusion granulation technique.

4. The solid pharmaceutical formulation as set forth in any one of the above 1 to 3, wherein the starting starch is a corn starch.

5. The solid pharmaceutical formulation as set forth in any one of the above 1 to 4, which is in the form of a granule or a powder.

6. The solid pharmaceutical formulation as set forth in any one of the above 1 to 5, which is in the form of a sustained release preparation.

7. The solid pharmaceutical formulation as set forth in any one of the above 1 to 6, wherein the active medical ingredient is a medicament hardly soluble in water.

8. The solid pharmaceutical formulation as set forth in any one of the above 1 to 7, wherein the active medical ingredient is a medicament classified into Class II in Biopharmaceutics Classification System.

9. The solid pharmaceutical formulation as set forth in any one of the above 1 to 8, wherein the active medical ingredient is cilostazol.

10. A solid pharmaceutical formulation, which is prepared by the following steps (i) and (ii):
   (i) a step of mixing an active medical ingredient and a starting usual starch to prepare a starting composition, and
   (ii) a step of subjecting the starting composition to a pre-gelatinization of starch.

11. The solid pharmaceutical formulation as set forth in the above 10, which contains a pre-gelatinized starch in an amount of 10 to 90% by weight based on the whole weight of the formulation.

12. The solid pharmaceutical formulation as set forth in the above 10 or 11, wherein the starting composition prepared in the step (i) further comprises crystalline cellulose and is granulated by an extrusion granulation technique.

13. The solid pharmaceutical formulation as set forth in any one of the above 10 to 12, wherein the starting starch is a corn starch.

14. The solid pharmaceutical formulation as set forth in any one of the above 10 to 13, which is in the form of a granule or a powder.

15. The solid pharmaceutical formulation as set forth in any one of the above 10 to 14, which is in the form of a sustained release preparation.

16. The solid pharmaceutical formulation as set forth in any one of the above 10 to 15, wherein the active medical ingredient is a medicament hardly soluble in water.

17. The solid pharmaceutical formulation as set forth in any one of the above 10 to 16, wherein the active medical ingredient is a medicament classified into Class II in Biopharmaceutics Classification System.

18. The solid pharmaceutical formulation as set forth in any one of the above 10 to 17, wherein the active medical ingredient is cilostazol.

The present invention further includes the following features as a method for preparing a solid pharmaceutical formulation.

19. A method for preparing a solid pharmaceutical formulation which comprises the following steps (i) and (ii):
   (i) a step of mixing an active medical ingredient and a starting usual starch to prepare a starting composition, and
   (ii) a step of subjecting the starting composition to a pre-gelatinization of starch.

20. The method as set forth in the above 19, which further comprises a drying step (iii) after the step (ii).

21. The method as set forth in the above 19 or 20, wherein the starting composition prepared in the step (i) is prepared by mixing an active medical ingredient, a usual starch and a crystalline cellulose and is subjected to granulation by an extrusion granulation technique.

22. The method as set forth in any one of the above 19 to 21, wherein the solid pharmaceutical formulation contains a pre-gelatinized starch in an amount of 10 to 90% by weight based on the whole weight of the formulation.

23. The method as set forth in any one of the above 19 to 22, wherein the starting starch is a corn starch.

24. The method as set forth in any one of the above 19 to 23, wherein the solid pharmaceutical formulation is in the form of a granule or a powder.

25. The method as set forth in any one of the above 19 to 24, wherein the solid pharmaceutical formulation is in the form of a sustained release preparation.

26. The method as set forth in any one of the above 19 to 25, wherein the active medical ingredient is a medicament hardly soluble in water.

27. The method as set forth in any one of the above 19 to 26, wherein the active medical ingredient is a medicament classified into Class II in Biopharmaceutics Classification System.

28. The method as set forth in any one of the above 19 to 27, wherein the active medical ingredient is cilostazol.

BEST MODE FOR CARRYING OUT THE INVENTION

Figure 1:
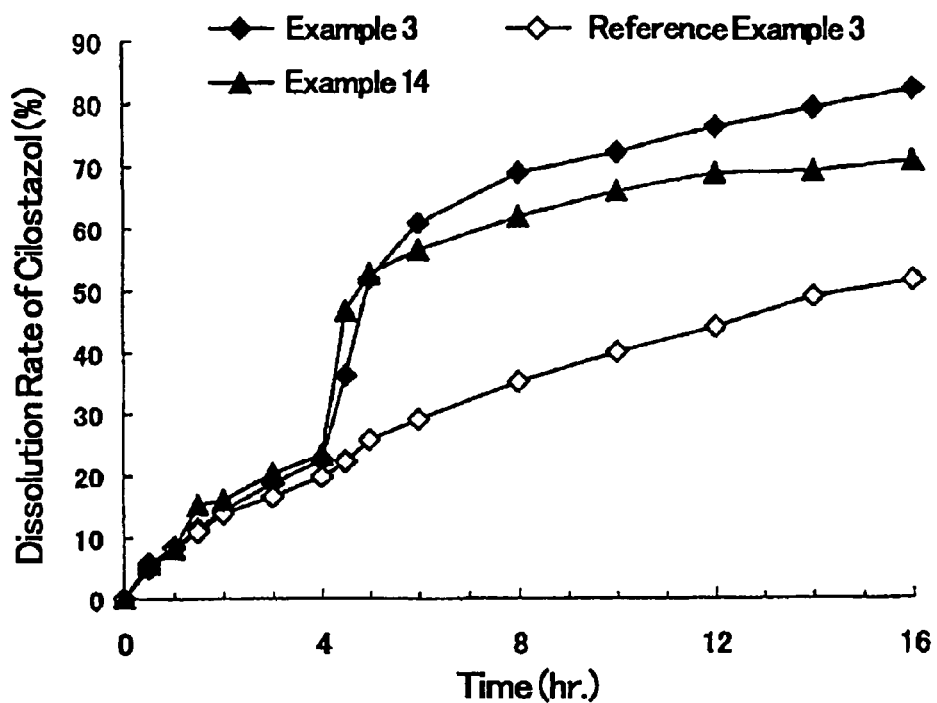
FIG. 1 is a graph showing dissolution characteristics of the solid pharmaceutical formulations (in Examples 3 and 14 and Reference Example 4) which was measured in Experiment 2.

The solid pharmaceutical formulation and the method for preparing thereof are described in detail below.

Solid Pharmaceutical Formulation

The solid pharmaceutical formulation of the present invention comprises (a) an active medical ingredient and (b) a pre-gelatinized starch.

The solid pharmaceutical formulation of the present invention contains usually 10 to 90% by weight, preferably 20 to 80% by weight, more preferably 30 to 70% by weight, of the pre-gelatinized starch (α-starch) based on the whole weight of the formulation. By incorporating the pre-gelatinized starch in such a range of amount, the solid pharmaceutical formulation of the present invention has the desired characteristics such as high physical strength of the formulation and the desired effective and sustained release of the active ingredient within the digestive tract when administered.

The starting starch to be used is not limited but includes any conventional starches such as corn starch, wheat starch, potato starch, rice starch, cassaya starch, tapioca starch, which may be used in a single kind of the starches or in combination of two or more starches. These starches are pre-gelatinized during the preparation of the solid formulation, particularly in the form of a pharmaceutical composition mixing with the active ingredient and other pharmaceutical carriers. Thus, the solid pharmaceutical composition of the present invention contains a pre-gelatinized starch obtained by pre-gelatinizing the above conventional starches. The pre-gelatinized starch may be the one partly pre-gelatinized. The pre-gelatinized starch in this description means a product which become pasty when water is added thereto (cf. Japanese Pharmaceutical Excipients, issued by YAKUJI NIPPO, LTD., Aug. 8, 2003, pp. 90-91)

Preferred pre-gelatinized starches are a pre-gelatinized corn starch, a pre-gelatinized potato starch, and a pre-gelatinized wheat starch. Particularly preferred pre-gelatinized starch is a pre-gelatinized corn starch, because the conventional corn starch has a uniform particle size of 10 to 30 μm and hence is easily processed into the desired formulations and hence the pre-gelatinized product thereof is easily handled, and further because it has lower moisture-absorption characteristics in comparison with other starches.

The active medical ingredient to be incorporated into the solid pharmaceutical formulation of the present invention may be any kinds of medicaments having any pharmaceutical activities as far as they can be administered orally. They may be water-soluble medicaments or hardly water-soluble medicaments. Examples of the medicaments are medicaments to be incorporated in various pharmaceutical preparations such as agents for respiratory organs, agents for digestive organs, cardiovascular agents, agents for central nervous system, agents for peripheral nervous system, antibiotics, chemotherapeutics, antitumor agents, platelet aggregation inhibitors, anti-allergic agents, vitamins, or nutrients. Preferred medicaments are hardly water-soluble medicaments. Further preferred medicaments are classified into Class II (High Permeability, Law Solubility) in "Waiver of in Vivo Bioavailability and Bioequivalents Studies for Immediate Release Solids Dosage Forms Containing Certain Active Moieties/Active Ingredients Based on Biopharmaceutics Classification System (FDA Guidance)" (in this description, it may occasionally be referred to as "Biopharmaceutics Classification System"). When the hardly water-soluble medicaments are formulated into a sustained release preparation, it can release the active medicament gradually and effectively within the digestive organs, and hence can exhibit the desired pharmaceutical activities when administered.

The medicaments may be used alone or in combination of two or more kinds of the medicaments.

Specific examples of the medicaments to be incorporated into the solid pharmaceutical formulation of the present invention are teophylline, grepafloxacin, carteolol, procaterol, rebamipide, aripiprazole, cilostazol, acetaminophen, nifedipine, ketoprophen, naproxen, diclofenac, itraconazole, piroxicam, phenytoin, or verapamil. Among them, preferred examples are cilostazol, ketoprophen, naproxen, diclofenac, itraconazole, piroxicam, phenytoin, and verapamil, and more preferred one is cilostazol. These medicaments are particularly useful when they are formulated in a sustained release preparation.

The medicaments may be incorporated into the solid pharmaceutical formulation in an appropriate amount, which may vary depending on the kinds and efficacy of the medicaments, sexes and ages of the patients to be treated, and so on, but may be, for example, in the range of about 0.01 to 60% by weight, preferably 0.1 to 50% by weight, more preferably 1 to 50% by weight, based on the whole weight (in dry weight) of the composition.

The solid pharmaceutical formulation may further be incorporated by an appropriate mount of various other additives such as excipients, binders, pH adjustors, disintegrators, absorption promoters, lubricants, colorants, flavors, perfumes, and the like, unless they give any adverse affect.

These additives are, for example, excipients (e.g. lactose, white sugar, mannitol, sodium chloride, glucose, calcium carbonate, kaolin, crystalline cellulose, silicates); binders (e.g. water, ethanol, simple syrup, aqueous glucose solution, aqueous starch solution, aqueous gelatine solution, carboxymethylcellulose, carboxymethylcellulose sodium, shellac, methyl cellulose, hydroxypropyl methylcellulose, hydroxypropyl cellulose, polyvinylpyrrolidone, polyvinyl alcohol, gelatin, dextrin, pullulan); pH adjustors (e.g. citric acid, citric anhydride, sodium citrate, sodium citrate dihydrate, anhydrous disodium hydrogenphosphate, anhydrous sodium dihydrogenphosphate, sodium hydrogenphosphate, sodium dihydrogen phosphate); disintegrators (e.g. carmellose calcium, low substituted hydroxypropylcellulose, carmellose, crosscarmellose sodium, carboxymethyl starch sodium, crosspovidone); plasticizers (e.g. polysorbate 80); absorption promoters (e.g. quaternary ammonium bases, sodium laurylsulfate); lubricants (e.g. purified talc, stearates, polyethylene glycol, colloidal silicates, sucrose fatty acid esters); colorants (e.g. yellow iron oxide, yellow iron sesquioxide, sesquioxide, (3-carotene, titanium oxide, food colors such as food blue No. 1, copper chlorophyll, riboflavin); flavors (e.g. ascorbic acid, aspartame, amacha, sodium chloride, fructose, saccharine, powdered sugar).

The solid pharmaceutical formulation of the present invention may be formulated in any type of solid formulations such as fine powders, powders, granules, tablets, or the like. The solid pharmaceutical formulation of the present invention may further be formulated in the form of coated products or capsules. Among these formulations, preferred ones are granules or powders.

In order to form in granules, it is preferable to incorporate crystalline cellulose into the solid pharmaceutical formulation. By incorporating crystalline cellulose, the composition can easily be formed in spherical shapes by conventional technique for regulating spherical shape, and hence, it is easily granulated by extrusion granulation technique. Besides, the composition is formed into spherical shape, it is easy to package into capsules. It is also advantageous that the spherical composition can effectively be coated. The crystalline cellulose may be incorporated in an amount of 5 to 90% by weight, preferably 10 to 80% by weight, more preferably 20 to 70% by weight, based on the whole weight of the pharmaceutical formulation.

The solid pharmaceutical formulation of the present invention can release the active medical ingredient gradually within the digestive tract. In addition, the pharmaceutical formulation is digested with amylase and thereby decomposed in the small intestine, by which the medical ingredient contained in the central area of the preparation can be sufficiently released by reaching to the lower passage of the digestive tract. Thus, according to the present invention, the pre-gelatinized starch is incorporated into the solid pharmaceutical formulation in the ratio as mentioned hereinbefore, and thereby, the solid pharmaceutical formulation satisfies both of the sustained release properties of the active ingredient and also the benefit of release of the medical ingredient with high efficiency within the digestive tract. Thus, the solid pharmaceutical formulation of the present invention can eliminate the defect of the conventional sustained release preparation that owing to the design of dissolving gradually in the digestive tract, the active medical ingredient is hardly dissolved out at lower part of the digestive tract (i.e. after passing intestine) having less amount of aqueous liquid (digestive fluid) necessary for dissolving the ingredient and hence the preparation is excreted out of the body without sufficiently dissolving and releasing the active ingredient.

Method for Preparation

The solid pharmaceutical formulation of the present invention can be prepared by subjecting a composition comprising an active medical ingredient and a usual starch as a binder and optionally other conventional carriers (e.g. the starting composition) to pre-gelatinization. That is, the solid pharmaceutical formulation can be prepared by the following steps (i) and (ii):

(i) a step of mixing an active medical ingredient and a starting usual starch and optionally other conventional carrier to prepare a starting composition, and (ii) a step of subjecting the starting composition to a pre-gelatinization of starch.

The components contained in the starting composition prepared in the step (i) are remained as they stand in the final solid pharmaceutical formulation except the starch which is pre-gelatinized to be converted into α-starch in the step (ii). Accordingly, in the step (i), the active medical ingredient, the starch to be pre-gelatinized, and other optional components (various carriers) may be incorporated for preparing the starting composition in the same amounts as those in the final solid pharmaceutical formulation.

The starting composition contains preferably water in addition to the above-mentioned components. The water content in the starting composition is not limited to specific range, but is usually 30 to 80% by weight, preferably 40 to 80% by weight, more preferably 40 to 70% by weight, based on the whole weight of the starting composition. By incorporating water in such a range as mentioned above, the starting composition can easily be formed into the desired forms and further can be subjected to the subsequent pre-gelatinization step effectively.

The starting composition may be any types of solid compositions, such as fine powders, powders, granules, tablets, and so on. The shape of the starting composition can be maintained even after being subjected to the pre-gelatinization in the step (ii) to form the desired solid pharmaceutical formulation containing the pre-gelatinized starch (α-starch) with the same shape. Accordingly, the starting composition is preferably formed in the same formulation form as the final product suitable for the desired drug.

The method for formulation of the starting composition into the desired forms is not limited but it may be prepared by a conventional method. When the solid pharmaceutical formulation is in the form of the granules, it is preferable to incorporate crystalline cellulose into the starting composition and to granulate the composition by extrusion granulation technique in the step (i).

The starting composition thus obtained is subjected to the next step (ii), wherein the usual starch is pre-gelatinized so as to be converted into α-starch. The pre-gelatinization may be carried out by a conventional method for converting usual starch into α-starch. For example, when the starting composition contains water as mentioned above, the starting composition is subjected to heat treatment. The heat treatment may be carried out by any conventional heating treatment, for example, heating with steam, dry heating with hot air, high frequency induction heating, heating with microwave, and the like. The heating temperature may vary according to the heating means, but is usually in the range of 75 to 100° C., preferably 80 to 100° C. The heating time may appropriately be determined according to the heating means by a person skilled in the art.

Besides, when the starting composition does not contain water, the starting composition is preferably subjected to heating with steam, for example, by spraying water onto the starting composition and then treating with a steam microwave, by which the starch is converted into α-starch. The heating conditions are the same as mentioned above.

When the starting composition contains crystalline cellulose and is in the form of granules prepared with extrusion granulation technique, the granules have uniform spherical shape (high degree of spherical shape), and hence, are suitably subjected to microwave heating. When the starting composition having spherical shape of not flat (concavo-convex) surface is subjected to the heating with microwave, the parts having convex surface are first heated and the moisture is distilled off from the surface, and thereby the pre-gelatinization is done with less efficiency. On the other hand, when the starting composition having spherical shape in high degree is subjected to heating with microwave, the starting composition is heated first from inner part and hence the surface keeps the moisture with less evaporation during the heating treatment, and thereby, the pre-gelatinization can effectively be done. Besides, the pre-gelatinization may also be done by heating with steam.

Thus, the starting composition is subjected to the pre-gelatinization of the starch contained in the composition to give the desired formulation containing pre-gelatinized starch (α-starch). The resulting pharmaceutical formulation thus pre-gelatinized contains moisture and hence is preferably subjected to drying in order to remove the moisture. The drying is carried out by a conventional method, for example, by keeping in a drying room at a temperature of 50 to 90° C., preferably 60 to 80° C. The drying time may optionally be determined depending on the forms of the pharmaceutical formulation and the drying temperature, and so on by a person skilled in the art.

The solid pharmaceutical formulation of the present invention may be the preparation obtained by the above steps (i) and (ii) and optionally further drying step, i.e. the preparation obtained by the pre-gelatinization, or alternatively it may be a preparation obtained by subjecting the solid formulation obtained by the pre-gelatinization to a further processing step by any conventional methods which are usually used for preparing pharmaceutical formulations.

For example, the granules obtained by pre-gelatinization are subjected to tableting to give a solid pharmaceutical formulation in the form of tablets. Besides, the solid pharmaceutical formulation or a further processed product is subjected to coating to give a coated product. Further, the solid pharmaceutical formulation or a further processed product is packed into capsules to give the desired solid pharmaceutical formulation in the form of capsules.

Effects of Invention

The solid pharmaceutical formulation of the present invention has high physical strength and can easily be obtained in a high yield with less break or decomposition during the preparation steps.

Besides, the solid pharmaceutical formulation of the present invention has excellent characteristics of releasing efficiently within the digestive organs with sustained release properties and hence can exhibit the desired pharmacological activities when administered, while it has high physical strength.

Moreover, the solid pharmaceutical formulation of the present invention comprises as an excipient a pre-gelatinized starch (α-starch) which is decomposed by an amylase within the digestive tract and hence is excellent in digestibility.

Furthermore, the present invention provides a method for preparing easily the solid pharmaceutical formulation comprises as an excipient a pre-gelatinized starch (α-starch) which has hardly been obtained by a conventional method.

BEST MODE FOR CARRYING OUT THE INVENTION

The present invention is illustrated in more detail by the following examples and experiments, but should not be construed to be limited thereto.

Example 1

Corn starch (tradename, "Nisshoku Corn Starch", manufactured by Nippon Shokuhin Kako K.K.) (210 g), crystalline cellulose (tradename, "Avicel PH-301", manufactured by Asahi Kasei Corporation) (30 g), and cilostazol (manufactured by Otsuka Pharmaceutical Co., Ltd.) (60 g) were mixed and the mixture was entered into a speed kneader (Model number: NSK-150, manufactured by Okada Seiko K.K.), and thereto a purified water (160 g) was added with stirring to give a starting mixture (Starting Mixture Example 1).

The starting mixture was subjected to extrusion granulation with an extrusion granulator equipped with a dome die (hole diameter, 0.6 mm) (DomeGran DG-L1, manufactured by Fuji Powdal Co.) to give wet granules. The wet granules were treated with a spheroidizer (Murmerizer QJ-400, manufactured by Fuji Paudal) to regulate the shape and size of the granules, by which the starting composition of wet granules (Starting Composition Example 1) was obtained.

The starting composition of wet granules was subjected to heating with steam with a steam oven (Model number: NE-J630, manufactured by Matsushita Electric Industrial Co., Ltd.) at 700 W for 6 minutes, by which the corn starch was pre-gelatinized. The granules thus heated with steam were dried within a drying oven at 60° C. for 6 hours to give a solid pharmaceutical formulation in the form of granules containing 20% by weight of cilostazol (Formulation Example 1).

Reference Preparation 1

Pre-gelainized corn starch (tradename, "Amycol", manufactured by Nichiden Kagaku K.K.) (210 g), crystalline cellulose (tradename, "Avicel PH-301", manufactured by Asahi Kasei Corporation) (30 g), and cilostazol (manufactured by Otsuka Pharmaceutical Co., Ltd.) (60 g) were mixed and the mixture was entered into a speed kneader (Model number: NSK-150, manufactured by Okada Seiko K.K.), and thereto a purified water (160 g) was added with stirring. As the result, the mixture became a sticky, soft candy-like material within the kneader, and hence, the resulting material could not be used for preparing the desired preparation.

Reference Example 1

Without subjecting to pre-gelatinization treatment, the starting composition of wet granules (Starting Composition Example 1) was directly dried within a drying oven at 60° C. for 6 hours to give a solid pharmaceutical formulation in the form of granules containing 20% by weight of cilostazol (Reference Formulation Example 1).

Examples 2 to 11

The starch, crystalline cellulose and drug as shown in Tables 1 and 2 were mixed and the mixture was entered into a speed kneader (Model number: NSK-150, manufactured by Okada Seiko K.K.), and thereto a purified water (150-220 g) was added with stirring to give starting compositions (Starting Composition Examples 2 to 11).

The starting compositions were subjected to extrusion granulation with an extrusion granulator equipped with a dome die (hole diameter, 0.6 mm) (DomeGran DG-L1, manufactured by Fuji Powdal Co.) to give wet granules. The wet granules were treated with a spheroidizer (Murmerizer QJ-400, manufactured by Fuji Paudal) to regulate the shape and size of the granules, by which the starting compositions of wet granules (Starting Composition Examples 2 to 11) were obtained.

The starting compositions of wet granules were subjected to heating with steam with a steam oven (Model number: NE-J630, manufactured by Matsushita Electric Industrial Co., Ltd.) at 700 W for 6 minutes, by which the starch was pre-gelatinized. The granules thus heated with steam were dried within a drying oven at 60° C. for 6 hours to give solid pharmaceutical formulations in the form of granules (Formulation Examples 2 to 11).

TABLE 1

| | | Starting Composition Examples | | | | | | |
|---|---|---|---|---|---|---|---|---|
| | | 2 | 3 | 4 | 5 | 6 | 7 | 8 |
| Starch | Corn starch | 150 g | 120 g | 30 g | 90 g | — | — | — |
| | Potato starch | — | — | — | — | 210 g | 120 g | 30 g |
| Crystalline cellulose | | 30 g | 120 g | 210 g | 150 g | 30 g | 120 g | 210 g |
| Cilostazol | | 120 g | 60 g | 60 g | 60 g | 60 g | 60 g | 60 g |

TABLE 2

| | | Starting Composition Examples | | |
|---|---|---|---|---|
| | | 9 | 10 | 11 |
| Starch | Corn starch | 30 g | 120 g | 210 g |
| | Potato starch | — | — | — |
| Crystalline cellulose | | 210 g | 120 g | 30 g |
| Drug | Phenytoin | 60 g | 60 g | 60 g |
| | Teophylline | — | — | 60 g |

Reference Examples 2 to 11

Without subjecting to pre-gelatinization treatment, the starting compositions of wet granules (Starting Composition Examples 2 to 11) were directly dried within a drying oven at 60° C. for 6 hours to give solid pharmaceutical formulations in the form of granules (Reference Formulation Examples 2 to 11).

Example 12

Corn starch (tradename, "Nisshoku Corn Starch", manufactured by Nippon Shokuhin Kako K.K.) (210 g), crystalline cellulose (tradename, "Avicel PH-301", manufactured by Asahi Kasei Corporation) (30 g), and cilostazol (manufactured by Otsuka Pharmaceutical Co., Ltd.) (60 g) were mixed and the mixture was entered into a vertical granulator (Model number: FM-VG-05P, manufactured by Powrex Co.), and thereto a purified water (160 g) was added with stirring and the mixture was granulated to give wet granules (Starting Composition Example 12).

The wet granules were subjected to heating with steam with a steam oven (Model number: NE-J630, manufactured by Matsushita Electric Industrial Co., Ltd.) at 700 W for 6 minutes, by which the corn starch was pre-gelatinized. The granules thus heated with steam were dried within a drying oven at 60° C. for 6 hours to give a solid pharmaceutical formulation in the form of granules containing 20% by weight of cilostazol (Formulation Example 12).

Example 13

The granules prepared in Reference Example 1 (20 g) were put on a wet filer paper (diameter, about 11 cm), and the surface of the granules was wetted by spraying water. The resulting wet granules were subjected to heating with steam with a steam oven (Model number: NE-J630, manufactured by Matsushita Electric Industrial Co., Ltd.) at 700 W for 3 minutes, by which the corn starch was pre-gelatinized. The granules thus heated with steam were dried within a drying oven at 60° C. for 6 hours to give a solid pharmaceutical formulation in the form of granules containing 20% by weight of cilostazol (Formulation Example 13).

Examples 14 and 15

The granules prepared in Reference Examples 3 and 7 (20 g) were treated in the same manner as described in Example 13 to give solid pharmaceutical formulations in the form of granules containing 20% by weight of cilostazol (Formulation Examples 14 and 15).

Examples 16 to 23

In the same manner as described in Examples 2 to 11 excepting that the materials as shown in Table 3 are used, the desired solid pharmaceutical formulations as shown in Table 3 (Formulation Examples 16 to 23) were prepared.

TABLE 3

| | Example | | | | | | | |
|---|---|---|---|---|---|---|---|---|
| | Ex. 16 | Ex. 17 | Ex. 18 | Ex. 19 | Ex. 20 | Ex. 21 | Ex. 22 | Ex. 23 |
| Corn starch (g) | 100 | 100 | 100 | 100 | 100 | 99 | 75 | 69 |
| crystalline cellulose (g) | 100 | 80 | 80 | 80 | 80 | 51 | 51 | 51 |
| Additives (g) | — | 20 a) | 20 b) | 20 c) | 20 d) | — | 24 d) | 30 d) |
| Cilostazol (g) | 100 | 100 | 100 | 100 | 100 | 150 | 150 | 150 | a) Acrylic copolymer (Eudragit L-30D55, manufactured by Röhm) (indicated by amount of LD solid content)
b) Ethyl acrylate/methyl methacrylate copolymer (Eudragit NE30D, manufactured by Rohm) (indicated by amount of solid content)
c) Ethylcellulose (Aquacoat, manufactured by Asahi Kasei Corp.) (indicated by amount of solid content)
d) Alpha-starch (Amycol, manufactured by Nichiden Kagaku K.K.)

Reference Examples 16 to 23

Without subjecting to pre-gelatinization treatment, the starting compositions of wet granules (prepared in the procedure in Examples 16 to 23) were directly dried within a drying oven at 60° C. for 6 hours to give solid pharmaceutical formulations in the form of granules (Reference Formulation Examples 16 to 23).

Experiment 1

Evaluation of Strength of the Formulations

With respect to the solid pharmaceutical formulations in the form of granules of Examples 1 to 2 and Reference Examples 1 to 2, the strength of formulation was measured by using one granule thereof (diameter, about 0.6 mm) (n=3) with Shimadzu AutoGraph (Model number: AG-1, manufactured by Shimadzu Corporation). The results are shown in Table 4. In the table, the strength is indicated by the load (N) which was given to the formulation (granule) when the granule was broken.

As is clear from the experimental results, the solid pharmaceutical formulations of Examples 1 to 2 showed 2 to 3 times higher strength of formulation in comparison with those of Reference Examples 1 to 2, which shows that the physical strength of formulation would remarkably be increased by pre-gelatinization of starch.

TABLE 4

| | Example 1 | Example 2 | Ref. Ex. 1 | Ref. Ex. 2 |
|---|---|---|---|---|
| Strength (N) | 18.0 | 12.7 | 9.3 | 4.3 |

Experiment 2

Evaluation of Drug Release Properties

With respect to the solid pharmaceutical formulations in the form of granules of Examples 3 and 14 and Reference Example 3, the drug release properties were evaluated. Specifically, according to Paddle method for testing dissolution (50 r.p.m.) as disclosed in Japanese Pharmacopoeia, Dissolution Test, 2nd Method, the rate of dissolved cilostazol from the formulation (dissolution rate, %) was measured by using the solid pharmaceutical formulations in the form of granules (500 mg) (Examples 3 and 14 and Reference Example 3) and 0.3 wt. % aqueous sodium laurylsulfate solution (900 mL) as an eluting solvent, wherein the amount of cilostazol eluted with lapse of time was measured.

In this test, amylase (activity, 20 units/mg or higher, tradename: "α-Amylase", manufactured by Wako Pure Chemical Industries, Limited) (0.18 g) was added to the dissolved liquid four hours after starting the test for the purpose of assimilating to the liquid within digestive tract.

The results are shown in the accompanying FIG. 1. As is seen from the experimental results, the formulations of Examples 3 and 14 and Reference Example 3 showed similar dissolution behavior until amylase was added. On the other hand, after adding amylase, the formulations of Examples 3 and 14 showed significantly increased dissolution rate, but the formulation of Reference Example 3 showed no change in drug dissolution rate even after adding amylase.

From the above experimental results, it was confirmed that the solid pharmaceutical formulations of the present invention have properties of rapidly dissolving (releasing) the drug due to action of amylase in digestive tract, particularly when reached to the digestive tract lower than small intestine.

Experiment 3

Evaluation of Drug Release Properties (2)

With respect to the solid pharmaceutical formulations in the form of granules of Example 9 and Reference Example 9, the drug release properties were evaluated. Specifically, according to Paddle method for testing dissolution (50 r.p.m.) as disclosed in Japanese Pharmacopoeia, Dissolution Test, 2nd Method, the rate of dissolved cilostazol from the formulation (dissolution rate, %) was measured by using the solid pharmaceutical formulations in the form of granules (250 mg) (Example 9 and Reference Example 9) and 0.5 wt. % aqueous sodium laurylsulfate solution (900 mL) containing amylase (activity, 20 units/mg or higher, tradename: "α-Amylase", manufactured by Wako Pure Chemical Industries, Limited) (0.09 g) as an eluting solvent, wherein the amount of eluted phenytoin after 4 hours from the starting of the test was measured. Besides, for comparison purpose, the above procedure was repeated except that the eluting solvent containing no amylase was used, and the rate of eluted phenytoin (dissolution rate (%)) was measured likewise.

The results are shown in the following Table 5. As is seen from the experimental results, the dissolution rate of phenytoin in the formulation of Reference Example 9 showed similar to each other in the cases of the eluting solvents containing amylase or containing no amylase. On the other hand, with respect to the formulation of Example 9, in case of the eluting solvent containing no amylase, the dissolution rate of phenytoin was similar to that in the formulation of Reference Example 9, but in case of the eluting solvent containing amylase, the formulation of Example 9 showed significantly increased dissolution rate, and thereby it was confirmed that the solid pharmaceutical formulations of the present invention have properties of rapidly dissolving (releasing) the drug due to action of amylase in digestive tract, particularly when reached to the digestive tract lower than small intestine.

TABLE 5

| | Dissolution rate of Phenytoin | | Difference in dissolution |
|---|---|---|---|
| | Without amylase (a) | With amylase (b) | rate between with and without amylase [(b) − (a)] (%) |
| Example 9 | 37.2 | 62.1 | 24.9 |
| Ref. Ex. 9 | 33.8 | 38.4 | 4.6 |

Experiment 4

Evaluation of Pharmacokinetics

The granules containing 20 wt. % of cilostzol prepared in Example 3 and Reference Example 3 (500 mg; converted into cilostazol, 100 mg) was orally administered to beagle dogs (four) during the fasting state, and the blood was collected with lapse of time, and the concentration of cilostazol in the collected blood was measured. Besides, as to the granules prepared in Example 3, it was also tested by administering the test product to the animals after feeding (n=4) and the concentration of cilostazol was measured likewise.

Separately, a commercially available Pretal Tablet® (corresponding to cilostazol 100 mg, in admixture with crystalline cellulose, corn starch, carmellose calcium, hydroxypropyl methylcellulose, and magnesium stearate) (Reference Example 13) was orally administered to the animals, and the blood was collected with lapse of time, and the concentration of cilostazol in the collected blood was measured (n=4).

Figure 2:
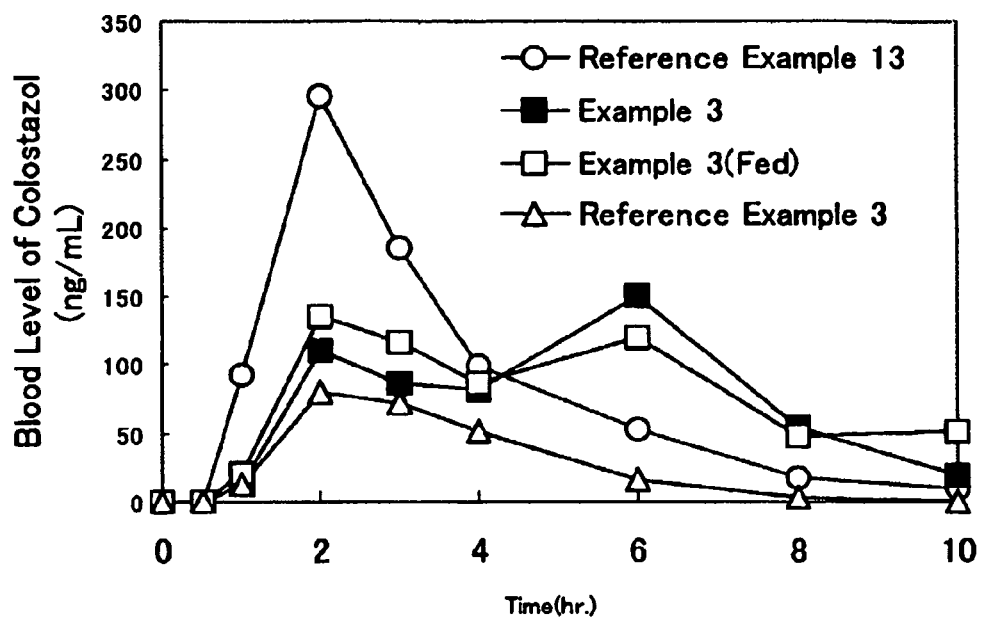
FIG. 2 is a graph showing change of average blood level of cilostazol with time as to the solid pharmaceutical formulations (in Example 3, Example 3 (Fed.) and Reference Examples 3 and 13) which was measured in Experiment 4, said Example 3 (Fed) meaning that the test drug was administered after feeding.

The change of blood level of cilostazol was compared as shown in the accompanying FIG. 2, wherein Example 3 (Fed) means that the test product was administered to the animals after feeding. Further, the parameters of pharmacokinetics (average±SD) are shown in Table 6.

TABLE 6

| | AUCt (ng · hr/mL) | AUC∞ (ng · hr/mL) | Cmax (ng/mL) |
|---|---|---|---|
| Example 3 | 761 ± 274 (89%) | 824 ± 286 (94%) | 172 ± 72 (57%) |
| Example 3 (Fed) | 784 ± 131 (92%) | 1030 ± 202 (116%) | 169 ± 15 (56%) |
| Ref. Ex. 3 | 277 ± 146 (33%) | 326 ± 173 (37%) | 113 ± 101 (37%) |
| Ref. Ex. 13 | 852 ± 556 (100%) | 879 ± 570 (100%) | 302 ± 190 (100%) |

In the table, the rate of the parenthesized data (%) is the ratio to the value of Reference Example 13 (100%). Besides, the abbreviated terms mean as follows.
AUCt: Area Under a Curve of correlation between the blood level and elapse of time (in trapezoidal rule)
AUC∞: Area Under a Curve of correlation between the blood level and elapse of time till infinite time
Cmax: Maximum blood level As is clear from Table 6, the formulation of Reference Example 3 could inhibit Cmax compared with the formulation of Reference Example 13, but it lowered also AUC. Thus, the formulation of Reference Example 3 lowered merely the release of the drug. On the other hand, the formulation of Example 3 of the present invention could inhibit well the Cmax by 57% in comparison with the product of Reference Example 13 (commercially available "Pretal Tablet") but could maintain the AUC∞ by 94%, which means that the formulation of the present invention can exhibit excellent sustained release properties.

Moreover, as is clear from FIG. 2, the formulation of Reference Example 3 lowered the blood level of cilostazol after 2 hours, which means that the formulation has less drug release properties within the digestive tracts. On the other hand, the formulation of Example 3 showed continuous release of cilostazol within the digestive tract and thereby the desired blood level of cilostazole is continuously maintained. When the product of Example 3 was administered to the animals after feeding, the concentration of cilostazol in blood remained at a similar level to that of the case where the test product was administered during the fasting state, and no significant change was observed in the parameters of pharmacokinetics. Thus, the pharmacokinetics of the product of the present invention is almost not affected by diet.

Experiment 5

Evaluation of Pharmacokinetics (2)

In the same manner as described in Experiment 4, the pharmacokinetics of the granules prepared in Example 23 and Reference Example 23 were tested.

Figure 3:
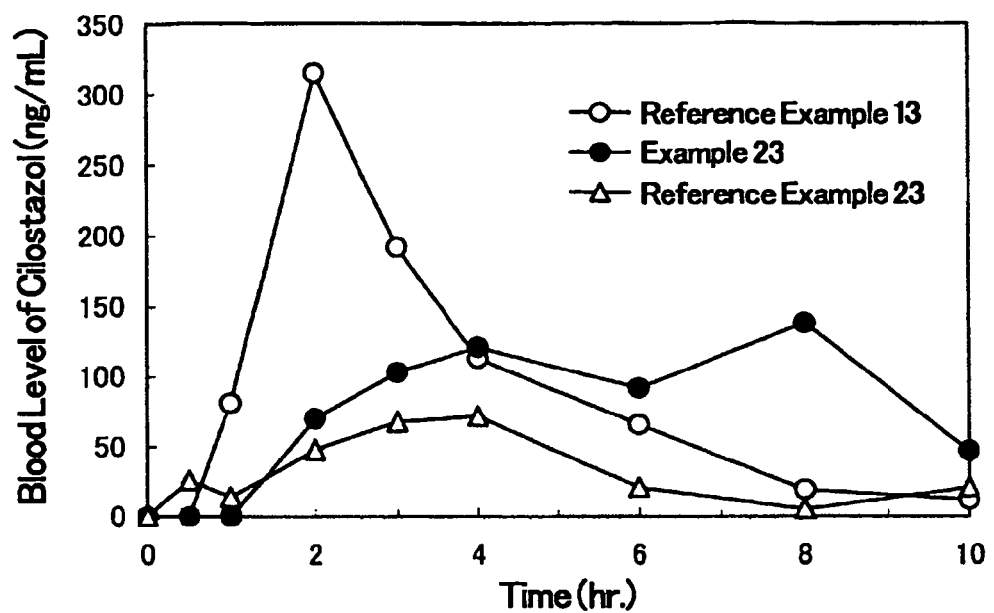
FIG. 3 is a graph showing change of average blood level of cilostazol with time as to the solid pharmaceutical formulations (in Example 23 and Reference Examples 23 and 13) which was measured in Experiment 5.

The change of blood level of cilostazol was compared as shown in the accompanying FIG. 3, and further, the parameters of pharmacokinetics (average±SD) are shown in Table 7.

TABLE 7

| | AUCt (ng·hr/mL) | AUC∞ (ng·hr/mL) | Cmax (ng/mL) |
|---|---|---|---|
| Example 23 | 861 ± 192 (94%) | 968 ± 279 (102%) | 212 ± 24 (66%) |
| Ref. Ex. 23 | 322 ± 211 (35%) | 471 ± 351 (50%) | 106 ± 71 (33%) |
| Ref. Ex. 13 | 916 ± 663 (100%) | 947 ± 678 (100%) | 322 ± 227 (100%) |

In the table, the rate of the parenthesized data (%) is the ratio to the value of Reference Example 13 (100%). Besides, the abbreviated terms are as mentioned in the above Table 6.

As is clear from Table 7, the formulation of Reference Example 23 could inhibit Cmax compared with the formulation of Reference Example 13, but it lowered also AUC. Thus, the formulation of Reference Example 23 lowered merely the release of the drug. On the other hand, the formulation of Example 23 of the present invention could inhibit well the Cmax by 66% in comparison with the product of Reference Example 13 (commercially available "Pretal Tablet") but could maintain the AUC∞ in the same as in the commercially available product (102%), which means that the formulation of the present invention can exhibit excellent sustained release properties.

Moreover, as is clear from FIG. 3, the formulation of Reference Example 23 lowered the blood level of cilostazol after 4 hours, which means that the formulation has less drug release properties within the digestive tracts. On the other hand, the formulation of Example 23 showed continuous release of cilostazol within the digestive tract and thereby the desired blood level of cilostazole is continuously maintained.

From the results of Experiments 4 and 5, it was confirmed that the solid pharmaceutical formulation of the present invention can release the desired drug within the digestive tract, and particularly that in case of hardly water soluble drugs having less dissolving properties at the region of less water like at lower digestive tract, the formulation of the invention can release the drug even after moving to digestive tract and it is useful for preparing in the form of a sustained release preparation.

INDUSTRIAL APPLICABILITY

The present invention provides a solid pharmaceutical formulation having high physical strength and further having excellent drug release properties and digestibility of the excipients when administered, which is prepared by using a cheap and stable usual starch as an excipient and then pre-gelatinizing the starting starch during the procedure for preparing the formulation.

The invention claimed is:

1. A solid pharmaceutical formulation which is in the form of a sustained release preparation comprising (a) cilostazol, (b) crystalline cellulose, and (c) a pre-gelatinized starch, which is prepared by the following steps:
    (i) mixing cilostazol, crystalline cellulose, starch, and water to prepare a starting composition, wherein the starch is selected from the group consisting of corn starch and potato starch;
    (ii) granulating the starting composition by an extrusion granulation technique to obtain wet granules;
    (iii) subjecting the wet granules to pre-gelatinization of the starch by heating with steam, wherein the heating temperature is 75 to 100° C.; and
    (iv) drying the heated granules to obtain the solid pharmaceutical formulation;
    wherein the solid pharmaceutical formulation contains pre-gelatinized starch in an amount of 10-90% by weight based on the weight of the solid pharmaceutical formulation.

2. The solid pharmaceutical formulation according to claim 1, wherein the starch is a corn starch.

3. The solid pharmaceutical formulation according to claim 1, wherein a pre-gelatinized starch is present in an amount of 20 to 80% by weight based on the weight of the solid pharmaceutical formulation.

4. The solid pharmaceutical formulation according to claim 1, wherein a pre-gelatinized starch is present in an amount of 30 to 70% by weight based on the weight of the solid pharmaceutical formulation.

5. A method for preparing a solid pharmaceutical formulation which is in the form of a sustained release preparation comprising (a) cilostazol, (b) crystalline cellulose, and (c) a pre-gelatinized starch, comprising the following steps:
    (i) mixing cilostazol, crystalline cellulose, starch, and water to prepare a starting composition, wherein the starch is selected from the group consisting of corn starch and potato starch;
    (ii) granulating the starting composition by an extrusion granulation technique to obtain wet granules;
    (iii) subjecting the wet granules to pre-gelatinization of the starch by heating with steam, wherein the heating temperature is 75 to 100° C.; and
    (iv) drying the heated granules to obtain the solid pharmaceutical formulation;
    wherein the solid pharmaceutical formulation contains pre-gelatinized starch in an amount of 10-90% by weight based on the weight of the solid pharmaceutical formulation.

* * * * *